US010351916B2

(12) United States Patent
Naidoo et al.

(10) Patent No.: US 10,351,916 B2
(45) Date of Patent: Jul. 16, 2019

(54) METHOD FOR IDENTIFICATION OF ANTI-HIV HUMAN MIRNA MIMICS AND MIRNA INHIBITORS AND ANTI-HIV PHARMACEUTICAL COMPOUNDS

(71) Applicant: CSIR, Pretoria (ZA)

(72) Inventors: Jerolen Naidoo, Pretoria (ZA); Samantha Barichievy, Moelndal (SE); Rethabile Khutlang, Johannesburg (ZA); Musa M Mhlanga, Johannesburg (ZA)

(73) Assignee: CSIR, Pretoria (ZA)

(*) Notice: Subject to any disclaimer, the term of this patent is extended or adjusted under 35 U.S.C. 154(b) by 0 days.

(21) Appl. No.: 15/962,645

(22) Filed: Apr. 25, 2018

(65) Prior Publication Data

US 2018/0251858 A1 Sep. 6, 2018

Related U.S. Application Data

(63) Continuation of application No. 15/105,029, filed as application No. PCT/IB2014/067019 on Dec. 17, 2014, now abandoned.

(30) Foreign Application Priority Data

Dec. 17, 2013 (ZA) ................................ 2013/09501

(51) Int. Cl.

| | |
|---|---|
| ***A61K 31/19*** | (2006.01) |
| ***C12Q 1/6886*** | (2018.01) |
| ***C12N 15/113*** | (2010.01) |
| ***A61K 38/12*** | (2006.01) |
| ***A61K 31/436*** | (2006.01) |
| ***A61K 31/437*** | (2006.01) |
| ***A61K 31/4439*** | (2006.01) |
| ***A61K 31/454*** | (2006.01) |
| ***A61K 31/475*** | (2006.01) |
| ***A61K 31/495*** | (2006.01) |
| ***A61K 31/496*** | (2006.01) |
| ***A61K 31/501*** | (2006.01) |
| ***A61K 31/5025*** | (2006.01) |
| ***A61K 31/506*** | (2006.01) |
| ***A61K 31/517*** | (2006.01) |
| ***A61K 31/519*** | (2006.01) |
| ***A61K 31/5377*** | (2006.01) |
| ***A61K 31/675*** | (2006.01) |

(Continued)

(52) U.S. Cl.

CPC .......... *C12Q 1/6886* (2013.01); *A61K 31/197* (2013.01); *A61K 31/436* (2013.01); *A61K 31/437* (2013.01); *A61K 31/4439* (2013.01); *A61K 31/454* (2013.01); *A61K 31/475* (2013.01); *A61K 31/4709* (2013.01); *A61K 31/495* (2013.01); *A61K 31/496* (2013.01); *A61K 31/501* (2013.01); *A61K 31/506* (2013.01); *A61K 31/5025* (2013.01); *A61K 31/517* (2013.01); *A61K 31/519* (2013.01); *A61K 31/5377* (2013.01); *A61K 31/58* (2013.01); *A61K 31/675* (2013.01); *A61K 31/7072* (2013.01); *A61K 31/713* (2013.01); *A61K 33/24* (2013.01); *A61K 38/12* (2013.01); *C12N 15/111* (2013.01); *C12N 15/1132* (2013.01); *C12Q 1/703* (2013.01); *C12N 2310/113* (2013.01); *C12N 2310/141* (2013.01); *C12N 2320/10* (2013.01); *C12N 2320/11* (2013.01); *C12N 2320/30* (2013.01); *C12Q 2600/136* (2013.01); *C12Q 2600/178* (2013.01)

(58) Field of Classification Search

CPC .............................. A61K 31/19; A61K 31/436
See application file for complete search history.

(56) References Cited

U.S. PATENT DOCUMENTS 6,297,245 B1 10/2001 Shaw
6,576,622 B1 * 6/2003 Strair .................... A61K 31/70 514/50

(Continued)

FOREIGN PATENT DOCUMENTS

CN 101974531 A 2/2011
EP 2546358 A1 1/2013

(Continued)

OTHER PUBLICATIONS

Makonkawkeyoon et al. CAS: 119: 108464, 1993.*

(Continued)

*Primary Examiner* — Rei Tsang Shiao
(74) *Attorney, Agent, or Firm* — McBee Moore Woodward & Vanik IP, LLC

(57) ABSTRACT

The present invention relates to methods for the identification of anti-HIV miRNAs and anti-HIV pharmaceutical compounds using high-throughput screening methods, comprising: transfecting reporter cells with a panel of miRNAs, infecting the reporter cells with HIV, screening the cells to identify miRNAs that modulate HIV infection and identifying the specific pathways, nucleic acids and/or polypeptides that are targeted by the miRNAs. The invention further provides for the identification and screening of anti-HIV pharmaceutical compounds having known activity against the specific pathways, nucleic acids and/or polypeptides that are targeted by the miRNAs for efficacy in the treatment of HIV. The invention also provides for the use of miRNA mimics, miRNA inhibitors and pharmaceutical compounds (including oncology drugs and kinase inhibitors) in the treatment and/or prevention of HIV infection.

22 Claims, 1 Drawing Sheet

Specification includes a Sequence Listing.

(51) Int. Cl.

| | |
|---|---|
| ***A61K 31/713*** | (2006.01) |
| ***A61K 33/24*** | (2019.01) |
| ***C12Q 1/70*** | (2006.01) |
| ***A61K 31/197*** | (2006.01) |
| ***A61K 31/4709*** | (2006.01) |
| ***A61K 31/58*** | (2006.01) |
| ***A61K 31/7072*** | (2006.01) |
| ***C12N 15/11*** | (2006.01) |

(56) References Cited

U.S. PATENT DOCUMENTS

| | | | |
|---|---|---|---|
| 2003/0138399 | A1 | 7/2003 | Anton et al. |
| 2007/0275963 | A1 | 11/2007 | Guzi et al. |
| 2008/0261978 | A1* | 10/2008 | Clark .................... C07C 237/30 514/235.8 |
| 2009/0176723 | A1 | 7/2009 | Brown et al. |
| 2009/0281167 | A1 | 11/2009 | Shen et al. |
| 2012/0088813 | A1 | 4/2012 | Buck |
| 2013/0096054 | A1 | 4/2013 | Kutsch et al. |
| 2014/0148499 | A1 | 5/2014 | Arnedo Valero et al. |

FOREIGN PATENT DOCUMENTS

| | | | |
|---|---|---|---|
| WO | 2007042899 | A2 | 4/2007 |
| WO | 2013134416 | A1 | 9/2013 |

OTHER PUBLICATIONS

Schmid et al. CAS: 145:277859, 2006.*

Vaccher et al. CAS: 135: 131873, 2001.*

Wang et al. CAS: 139:332602, 2003.*

Webber et al. CAS: 140: 317224, 2004.*

Deeken et al. CAS: 152: 110526, 2009.*

Anonymous, "miRIDIAN microRNA Mimics & Hairpin Inhibitors," Thermo Scientific Dharmacon 1-3 X Inv. C12Q/68 C12Q1/70 (Jan. 1, 2009), pp. 1-12.

Azuma-Mukai, Asuka, et al. "Characterization of endogenous human Argonautes and their miRNA partners in RNA silencing." Proceedings of the National Academy of Sciences 105.23 (2008): 7964-7969.

Baek, Daehyun, et al. "The impact of microRNAs on protein output." Nature 455.7209 (2008): 64.

Barbato, Christian, et al. "Computational challenges in miRNA target predictions: to be or not to be a true target?." BioMed Research International 2009 (2009).

Cecilia, D., et al. "Neutralization profiles of primary human immunodeficiency virus type 1 isolates in the context of coreceptor usage." Journal of virology 72.9 (1998): 6988-6996.

Cullen, Bryan R. "MicroRNAs as mediators of viral evasion of the immune system." Nature immunology 143 (2013): 205.

Ebert, Margaret S., and Phillip A. Sharp. "Roles for microRNAs in conferring robustness to biological processes." Cell 1493 (2012): 515-524.

Farh, Kyle Kai-How, et al. "The widespread impact of mammalian MicroRNAs on mRNA repression and evolution." Science 310. 5755 (2005): 1817-1821.

Fire, Andrew, et al. "Potent and specific genetic interference by double-stranded RNA in Caenorhabditis elegans." nature 391.6669 (1998): 806.

Genovesio, Auguste, et al. "Automated genome-wide visual profiling of cellular proteins involved in HIV infection." Journal of biomolecular screening 16.9 (2011): 945-958.

Hsu, Sheng-Da, et al. "miRTarBase: a database curates experimentally validated microRNA—target interactions." Nucleic acids research 39.suppl_1 (2010): D163-D169.

Lander et al., International SNP Map Working Group. "A map of human genome sequence variation containing 1.42 million single nucleotide polymorphisms." Nature 409.6822 (2001): 928.

Lee, Yoontae, et al. "MicroRNA genes are transcribed by RNA polymerase II" The EMBO journal 23.20 (2004): 4051-4060.

Lee, Yoontae, et al. "MicroRNA maturation: stepwise processing and subcellular localization." The EMBO journal 21.17 (2002): 4663-4670.

Lim, Lee P., et al. "Microarray analysis shows that some microRNAs downregulate large numbers of target mRNAs" Nature 433.7027 (2005): 769.

Liu, Jidong, et al. "Argonaute2 is the catalytic engine of mammalian RNAi." Science 305.5689 (2004): 1437-1441.

Martinez, Javier, and Thomas Tuschl. "RISC is a 5' phosphomonoester-producing RNA endonuclease." Genes & development 18.9 (2004): 975-980.

Mörner, Andreas, et al. "Primary human immunodeficiency virus type 2 (HIV-2) isolates, like HIV-1 isolates, frequently use CCR5 but show promiscuity in coreceptor usage." Journal of virology 73.3 (1999): 2343-2349.

Ponting, Chris P., and T. Grant Belgard. "Transcribed dark matter: meaning or myth?." Human molecular genetics 19.R2 (2010): R162.

Vlachos, Ioannis S., et al. "DIANA miRPath v. 2.0: investigating the combinatorial effect of microRNAs in pathways." Nucleic acids research 40.W1 (2012): W498-W504.

Yamada, Kayoko, et al. "Empirical analysis of transcriptional activity in the *Arabidopsis* genome." Science 302.5646 (2003): 842-846.

Yekta, Soraya, I-hung Shih, and David P. Bartel. "MicroRNA-directed cleavage of HOXB8 mRNA." Science 304.5670 (2004): 594-596.

Bradley A D et al., Altering Cell Death Pathways as an Approach to Cure HIV Infection, Cell Death and Disease, vol. 4 No. 7, 2013, e718.

Norio Fujiwara et al., Novel Piperidinylpyrimidine Derivatives as Inhibitors of HIV-1LTR Activation, Bioorganic & Medicinal Chemistry, vol. 16 No. 22, 2008, 9804-9816.

Okamoto et al., Potent Inhibition of HIV Type 1 Replication by an Antiinfiammatory Alkaloid, Cepharanthine, in Chronically Infected Monocytic Cells, Aids Research and Human Retroviruses, vol. 14, No. 4, 1998, 1239-1245.

Sadaie M et al., A Novel Approach to Develop Anti-HIV Drugs: Adapting Non-nucleoside Anticancer Chemotherapeutics, Antiviral Research, vol. 61 No. 1, 2004, 1-18.

Wang et al., Cellular microRNA expression correlates with susceptibility of monocytes/macrophages to HIV-1 nfection, Blood, Jan. 15, 2009 {published online Nov. 17, 2008), 671-74, vol. 113, No. 3.

Hong-Sheng Zhang et al., MiR-217 is involved in Tai-induced HIV-1 long terminal repeat {LTR) transactivation by down-regulation of S1RT1, Biochemica et Biphysica Acta, Mar. 3, 2012, 1017-23, vol. 1823.

Neil H. Tan Gana et al, MicroRNAs in HIV-1 infection: an integration of viral and cellular interaction at the Jenomic level, Frontiers in Microbiology, Aug. 24, 2012, 1-12, vol. 3, art. 306.

Huang et al. Nature Medicine 2007 1241-1247 (Year: 2007).

Nathans et al. Molecular Cell 34: 696-709 (Year: 2009).

* cited by examiner

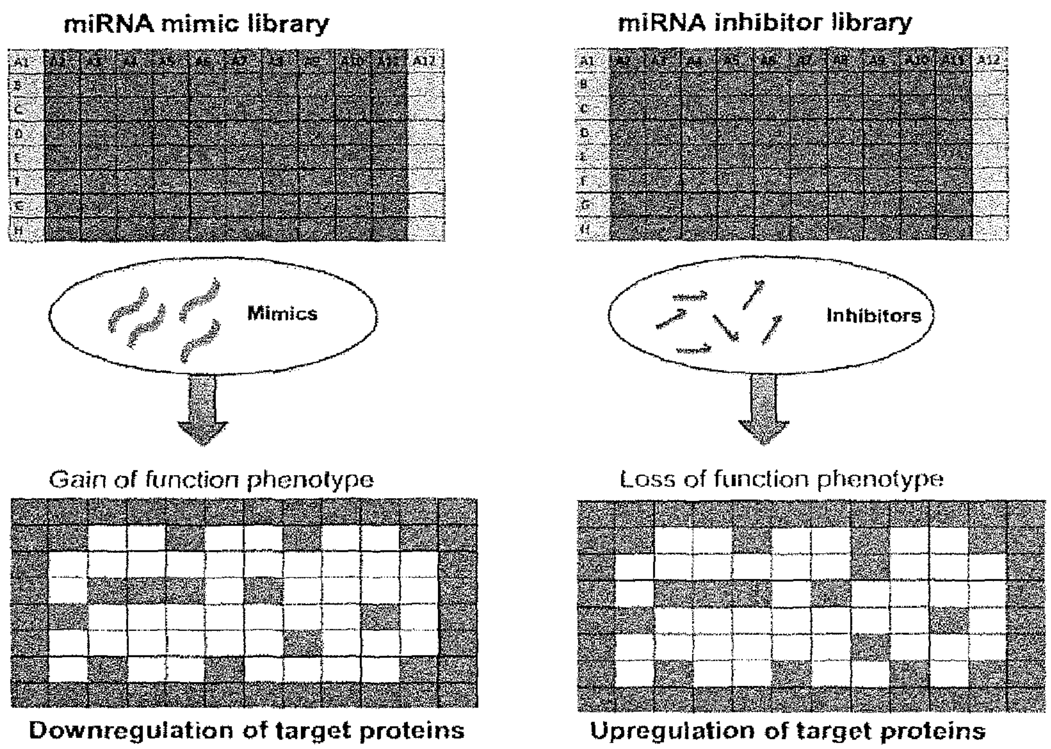
miRNA mimic library
miRNA inhibitor library
Mimics
Inhibitors
Gain of function phenotype
Loss of function phenotype
Downregulation of target proteins
Upregulation of target proteins

SEQUENCE LISTING

```
<160> NUMBER OF SEQ ID NOS: 35

<210> SEQ ID NO 1
<211> LENGTH: 22
<212> TYPE: RNA
<213> ORGANISM: Homo sapiens

<400> SEQUENCE: 1

ugagguagua gguuguauag uu                                    22


<210> SEQ ID NO 2
<211> LENGTH: 22
<212> TYPE: RNA
<213> ORGANISM: Homo sapiens

<400> SEQUENCE: 2
```

agagguagua gguugcauag uu 22

<210> SEQ ID NO 3
<211> LENGTH: 21
<212> TYPE: RNA
<213> ORGANISM: Homo sapiens

<400> SEQUENCE: 3
aucacauugc cagggauuuc c 21

<210> SEQ ID NO 4
<211> LENGTH: 22
<212> TYPE: RNA
<213> ORGANISM: Homo sapiens

<400> SEQUENCE: 4
ugaccgauuu cuccuggugu uc 22

<210> SEQ ID NO 5
<211> LENGTH: 22
<212> TYPE: RNA
<213> ORGANISM: Homo sapiens

<400> SEQUENCE: 5
aaucacuaac cacacggcca gg 22

<210> SEQ ID NO 6
<211> LENGTH: 23
<212> TYPE: RNA
<213> ORGANISM: Homo sapiens

<400> SEQUENCE: 6
agguugggau cgguugcaau gcu 23

<210> SEQ ID NO 7
<211> LENGTH: 20
<212> TYPE: RNA
<213> ORGANISM: Homo sapiens

<400> SEQUENCE: 7
uaaggcacgc ggugaaugcc 20

<210> SEQ ID NO 8
<211> LENGTH: 22
<212> TYPE: RNA
<213> ORGANISM: Homo sapiens

<400> SEQUENCE: 8
ucccugagac ccuaacuugu ga 22

<210> SEQ ID NO 9
<211> LENGTH: 23
<212> TYPE: RNA
<213> ORGANISM: Homo sapiens

<400> SEQUENCE: 9
agcugguguu gugaaucagg ccg 23

<210> SEQ ID NO 10
<211> LENGTH: 22
<212> TYPE: RNA
<213> ORGANISM: Homo sapiens

<400> SEQUENCE: 10
ugagaacuga auuccauggg uu 22

<210> SEQ ID NO 11
<211> LENGTH: 21
<212> TYPE: RNA
<213> ORGANISM: Homo sapiens

<400> SEQUENCE: 11
agggagggac gggggcugug c 21

<210> SEQ ID NO 12
<211> LENGTH: 22
<212> TYPE: RNA
<213> ORGANISM: Homo sapiens

<400> SEQUENCE: 12
ucucccaacc cuuguaccag ug 22

<210> SEQ ID NO 13
<211> LENGTH: 22
<212> TYPE: RNA
<213> ORGANISM: Homo sapiens

<400> SEQUENCE: 13
ucucccaacc cuuguaccag ug 22

<210> SEQ ID NO 14
<211> LENGTH: 23
<212> TYPE: RNA
<213> ORGANISM: Homo sapiens

<400> SEQUENCE: 14
uuaaugcuaa ucgugauagg ggu 23

<210> SEQ ID NO 15
<211> LENGTH: 22
<212> TYPE: RNA
<213> ORGANISM: Homo sapiens

<400> SEQUENCE: 15 cggggguuuug agggcgagau ga 22

<210> SEQ ID NO 16
<211> LENGTH: 23
<212> TYPE: RNA
<213> ORGANISM: Homo sapiens

<400> SEQUENCE: 16
uaauacugcc ggguaaugau gga 23

<210> SEQ ID NO 17
<211> LENGTH: 21
<212> TYPE: RNA
<213> ORGANISM: Homo sapiens

<400> SEQUENCE: 17
aggggugcua ucugugauug a 21

<210> SEQ ID NO 18
<211> LENGTH: 22
<212> TYPE: RNA
<213> ORGANISM: Homo sapiens

<400> SEQUENCE: 18
uuaucagaau cuccaggggu ac 22

<210> SEQ ID NO 19
<211> LENGTH: 23
<212> TYPE: RNA
<213> ORGANISM: Homo sapiens

<400> SEQUENCE: 19
aucaacagac auuaauuggg cgc 23

<210> SEQ ID NO 20
<211> LENGTH: 23
<212> TYPE: RNA
<213> ORGANISM: Homo sapiens

<400> SEQUENCE: 20
agcucggucu gaggccccuc agu 23

<210> SEQ ID NO 21
<211> LENGTH: 22
<212> TYPE: RNA
<213> ORGANISM: Homo sapiens

<400> SEQUENCE: 21
agacccuggu cugcacucua uc 22

<210> SEQ ID NO 22
<211> LENGTH: 22
<212> TYPE: RNA
<213> ORGANISM: Homo sapiens

<400> SEQUENCE: 22
ugauugguac gucugugggu ag 22

<210> SEQ ID NO 23
<211> LENGTH: 24
<212> TYPE: RNA
<213> ORGANISM: Homo sapiens

<400> SEQUENCE: 23
acugggggcu uucgggcucu gcgu 24

<210> SEQ ID NO 24
<211> LENGTH: 21
<212> TYPE: RNA
<213> ORGANISM: Homo sapiens

<400> SEQUENCE: 24
aggaggcagc gcucucagga c 21

<210> SEQ ID NO 25
<211> LENGTH: 20
<212> TYPE: RNA
<213> ORGANISM: Homo sapiens

<400> SEQUENCE: 25
cuacaaaggg aagcccuuuc 20

<210> SEQ ID NO 26
<211> LENGTH: 22
<212> TYPE: RNA

<213> ORGANISM: Homo sapiens

<400> SEQUENCE: 26
cuccugagcc auucugagcc uc 22

<210> SEQ ID NO 27
<211> LENGTH: 21
<212> TYPE: RNA
<213> ORGANISM: Homo sapiens

<400> SEQUENCE: 27
cggcggggac ggcgauuggu c 21

<210> SEQ ID NO 28
<211> LENGTH: 21
<212> TYPE: RNA
<213> ORGANISM: Homo sapiens

<400> SEQUENCE: 28
ccaguccugu gccugccgcc u 21

<210> SEQ ID NO 29
<211> LENGTH: 22
<212> TYPE: RNA
<213> ORGANISM: Homo sapiens

<400> SEQUENCE: 29
uuggggaaac ggccgcugag ug 22

<210> SEQ ID NO 30
<211> LENGTH: 23
<212> TYPE: RNA
<213> ORGANISM: Homo sapiens

<400> SEQUENCE: 30
uuagggagua gaaggguggg gag 23

<210> SEQ ID NO 31
<211> LENGTH: 23
<212> TYPE: RNA
<213> ORGANISM: Homo sapiens

<400> SEQUENCE: 31
agaagaaggc ggucggucug cgg 23

<210> SEQ ID NO 32
<211> LENGTH: 21
<212> TYPE: RNA
<213> ORGANISM: Homo sapiens

<400> SEQUENCE: 32 cccuugggguc ugaugggua g 21

<210> SEQ ID NO 33
<211> LENGTH: 23
<212> TYPE: RNA
<213> ORGANISM: Homo sapiens

<400> SEQUENCE: 33
uggggacgua gcuggccaga cag 23

<210> SEQ ID NO 34
<211> LENGTH: 22

-continued

```
<212> TYPE: RNA
<213> ORGANISM: Homo sapiens

<400> SEQUENCE: 34

caguuggguc uaggggucag ga                                              22


<210> SEQ ID NO 35
<211> LENGTH: 18
<212> TYPE: RNA
<213> ORGANISM: Homo sapiens

<400> SEQUENCE: 35

cucugggaaa ugggacag                                                   18
```

METHOD FOR IDENTIFICATION OF ANTI-HIV HUMAN MIRNA MIMICS AND MIRNA INHIBITORS AND ANTI-HIV PHARMACEUTICAL COMPOUNDS

CROSS-REFERENCE TO RELATED APPLICATIONS

This application is a continuation application of U.S. application Ser. No. 15/105,029, filed on Jun. 16, 2016, which is the U.S. national phase application filed under 35 U.S.C. § 371 claiming benefit to International Patent Application No. PCT/IB2014/067019, filed on Dec. 17, 2014, which is entitled to priority under 35 U.S.C. § 119(e) to ZA provisional application no. 2013/09501, filed Dec. 17, 2013, the disclosures of which are incorporated herein by reference in their entirety.

BACKGROUND OF THE INVENTION

The present invention relates to methods for the identification of anti-HIV miRNAs and anti-HIV pharmaceutical compounds using high-throughput screening methods, comprising: transfecting reporter cells with a panel of miRNAs, infecting the reporter cells with HIV, screening the cells to identify miRNAs that modulate HIV infection and identifying the specific pathways, nucleic acids and/or polypeptides that are targeted by the miRNAs. The invention further provides for the identification and screening of anti-HIV pharmaceutical compounds having known activity against the specific pathways, nucleic acids and/or polypeptides that are targeted by the miRNAs for efficacy in the treatment of HIV. The invention also provides for the use of miRNA mimics, miRNA inhibitors and pharmaceutical compounds in the treatment and/or prevention of HIV infection.

Humans display a remarkably diverse susceptibility to infection, the foundation of which lies in our genetic variation and ability to respond to selective pressures applied by various infectious agents. The evolution of our complex and multi-player immune system underlines the dominance of the human host following a microbial infection. However, given the nature of obligate intracellular pathogens, their complete reliance on host gene expression machinery has led to the evolution of complex interplays between the two, such that pathogens actively and strategically manoeuvre their way through the host terrain. Our traditional view of this terrain as being comprised of protein-coding genes, translation intermediates (mRNAs) and protein counterparts is far too simplistic, particularly in the context of infection. The discovery of the RNA interference (RNAi) pathway, for which the 2006 Nobel Prize was awarded, has greatly enhanced our understanding of the host terrain. Small non-coding RNAs (ncRNAs) termed microRNAs (miRNAs) were shown to be key regulators of gene expression that function within the RNAi pathway to post-transcriptionally modulate mRNA stability and subsequent translation (Fire et al., (1998)). Indeed, it is now understood that miRNAs are able to rapidly, and with exquisite specificity, modulate gene expression in response to numerous environmental cues in a highly coordinated, complex and tissue-specific manner. Given the reliance of intracellular pathogens on host gene expression machinery, the RNAi pathway, and specifically miRNAs, are now understood to lie at the nexus of the host-pathogen interplay.

Only 2% of the metazoan genome encodes protein, yet more than 50% is transcribed and we have little knowledge regarding these transcripts that function in the absence of protein production. In fact, stable ncRNA transcripts have been referred to as ‘dark matter’ within the cellular environment (Yamada et al., (2003)). Despite improvements in the human draft genome sequence, ncRNAs remain difficult to define and thus quantify (Ponting et al., (2010)). However, numerous evolutionary studies have revealed that ncRNAs are estimated to be expressed at 4-fold excess compared to their protein-coding counterparts and are highly conserved across eukaryotic genomes (Ponting et al., (2010)). Currently, ncRNAs have been classified by size into long ncRNAs (IncRNAs; >200 bp) or small ncRNAs (<200 bp) and comprise 26 or more functional categories reflecting something of the diversity of ncRNA function (Ponting et al., (2010)). In the case of humans, IncRNAs comprise about 48% of the genome (Lander et al., (2001)) while small ncRNAs including miRNAs, constitute a small but significant portion of the genome. While new ncRNAs are rapidly being uncovered, functional data remains sparse particularly at the host-pathogen interface. Endogenous miRNAs are usually transcribed from RNA polymerase II promoters (Lee et al., (2004)) as primary miRNA transcripts (pri-miRNAs) several kb in length, containing various stem-loop structures and ssRNA flanking segments. Pri-miRNAs are processed in two compartmentalized steps via the actions of distinct protein complexes (Lee et al., (2002)) to form mature miRNAs that regulate post-transcriptional protein synthesis by base pairing to cognate mRNAs. Depending on the degree of complementarity between the mature miRNA and its target, multiple mRNA silencing modes can occur (Azuma-Mukai et al., (2008)). The initial bases from positions 2 to 7 of the mature miRNA are termed the ‘seed’ sequence and they provide most of the pairing specificity. In some cases, complete pairing between the seed region and target mRNA is sufficient to mediate cleavage of the cognate mRNA (Liu et al., (2004); Yekta (2004)). More typically for mammalian and viral mRNA targets however, cleavage activity is severely impaired by mismatched pairing in the seed and other regions and translational inhibition occurs (Martinez and Tuschl (2004)). Intriguingly, since the complementary length of seed sequence required for miRNAs to target cognate mRNAs is short, each miRNA can target and modulate hundreds of transcripts. Indeed, current estimates predict that thousands of human transcripts are regulated by miRNAs (Farh et al., (2005); Lim et al., (2005)). Furthermore, a single miRNA can regulate multiple mRNA molecules that can in turn also be acted upon by numerous distinct miRNAs (Barbato et al., (2009)). Importantly, most miRNAs decrease target protein levels by less than 2-fold (Baek et al., (2008)), but this non-linear tuning mechanism can still exert a large physiological effect (Ebert and Sharp (2012)). Thus, the endogenous miRNA pathway represents a highly efficient system to simultaneously fine-tune the expression of numerous genes as well as modulate specific functional pathways.

Considering human cells encode >1000 miRNA species, many of which function in innate immunity, it is unsurprising that pathogens (and viruses in particular) have evolved mechanisms to subvert these cellular components (Cullen (2013)). The particular mechanisms by which viruses manipulate the host immune system are as varied as the viruses themselves but if one focuses on viral interactions with cellular microRNA machinery, the options are surprisingly minimized and constrained to a fairly limited number of human viruses. Furthermore, as miRNAs are expressed in a very tissue specific manner and can vary depending on the cell cycle stage, the interactions between host miRNAs and pathogens is clearly complex. The ability of a host organism to mount an innate immune response after pathogen infection is critical for survival and many cellular mRNAs that control host defences are regulated by miRNAs. The promiscuity of miRNAs in regulating their mRNA targets coupled with their importance in posttranscriptional regulation of host gene expression make unraveling the role of miRNAs at the host-pathogen interface extremely challenging. Resolving these interactions requires identification of the specific pathogen-encoded stimuli that induce changes in the host miRNome following infection, assessment of which transcripts are targeted by miRNAs as well as which miRNAs are responsible, quantification of the miRNA-induced changes to the infection transcriptome, analysis of downstream effects on related protein outputs, and validation of each step to ensure a robust understanding of such a complex network of interactions.

To identify host miRNAs required by the Human Immunodeficiency Virus (HIV-1) during infection, we conducted several genome-wide miRNA-based screens. We identified numerous host miRNAs that inhibit HIV-1 replication or enhance activation of the HIV long terminal repeat (LTR) promoter either when the specific miRNA is over-expressed (thus boosting expression levels of its endogenous miRNA sequence) or suppressed (thus 'sponging out' or quenching its endogenous miRNA sequence).

Based on extensive literature searches, the human mRNA targets of each of the HIV inhibitory miRNAs were identified. Intriguingly, many of these mRNA targets code for host proteins that play a role in the cellular response to DNA damage, repair and apoptosis. Given that these cellular pathways are central to the development and control of many cancers, we conducted additional validation experiments which have highlighted the close relationship between early HIV infection and abnormal cell survival phenotypes which are related to the DNA damage pathway and which are characteristic of many cancers. We thus sought to utilise compound libraries comprised of oncogenic and kinase-specific inhibitors, and tested for their ability to inhibit HIV infection. Several of the cancer-specific therapeutics inhibited HIV replication at targets and pathways analogous to those identified in the miRNA screens. Taken together our results have revealed novel host miRNAs as well as oncogenic compounds that can be repurposed for use in antiretroviral therapies targeted against HIV-1.

SUMMARY OF THE INVENTION

The present invention relates to a method for the identification of anti-HIV miRNAs and anti-HIV pharmaceutical compositions.

According to a first aspect of this invention there is provided for a method for the identification of anti-HIV miRNAs and anti-HIV pharmaceutical compounds, wherein the method comprises the steps of: a) providing a first batch of reporter cells and providing a panel of miRNAs, wherein the reporter cells are divided into a plurality of samples and wherein each sample is transfected with an miRNA from the panel, b) infecting the transfected cells with HIV, c) screening the samples to identify one or more (anti-HIV) miRNAs which modulate HIV infection from the panel of miRNAs, and d) identifying a specific cellular pathway, a polynucleotide and/or a polypeptide which is targeted by an anti-HIV miRNA from step c.

In one embodiment of the invention the method further comprises the steps of e) providing a second batch of reporter cells and providing a panel of pharmaceutical compounds with known pharmaceutical activity against the cellular pathways, the polynucleotides and/or the polypeptides of step d), wherein the second batch of reporter cells are divided into a plurality of samples and wherein each sample is treated with a pharmaceutical compound, f) infecting the second batch of reporter cells with HIV, wherein the step of infecting the second batch of reporter cells may occur before or after the treatment with the pharmaceutical compound; and g) identifying a pharmaceutical compound which has pharmaceutical activity against the specific cellular pathway, polynucleotide and/or polypeptide targeted by anti-HIV miRNA.

In one embodiment of the invention the miRNAs may be selected from miRNA mimics or miRNA inhibitors. Preferably, the miRNAs are human miRNAs.

In another embodiment of the invention an anti-HIV miRNAs which modulates HIV infection is selected from the group consisting of: i) anti-HIV miRNAs which are able to inhibit HIV entry into a cell, ii) anti-HIV miRNA molecules which are able to suppress activation of the HIV Long Terminal Repeat (LTR) promoter, iii) anti-HIV miRNA molecules which are able to sensitise uninfected cells to apoptosis in response to infection by HIV, and/or iv) anti-HIV miRNA molecules which are able to promote activation of the HIV LTR promoter.

In a further embodiment the anti-HIV miRNAs are selected from the group consisting of hsa-let-7a-5p, hsa-let-7d-5p, hsa-miR-23a, hsa-mir-29c*, hsa-miR-34c-3p, hsa-miR-92a-1-5p, hsa-mir-124a-3p, hsa-miR-124a, hsa-miR-125b-5p, hsa-miR-138, hsa-miR-146a, hsa-miR-149-3p, hsa-miR-150, hsa-miR-155. hsa-miR-193b-5p, hsa-miR-200c, hsa-miR-342-5p, hsa-miR-361-5p, hsa-miR-421, hsa-miR-423-3p, hsa-miR-504, hsa-miR-509-3p, hsa-miR-637, hsa-mir-650, hsa-miR-520d-5p, hsa-miR-1200, hsa-miR-1908, hsa-miR-1910, hsa-miR-2110, hsa-miR-3162, hsa-miR-3185, hsa-miR-3189, hsa-miR-3191, hsa-miR-3191-3p, hsa-miR-4259, and hsa-miR-4314.

In yet another embodiment of the invention the pharmaceutical compound of step g) may be selected from the group consisting of: i) pharmaceutical compounds which are selectively toxic to cells infected with HIV, ii) pharmaceutical compounds which are able to sensitize uninfected cells to apoptosis in response to infection by HIV, iii) pharmaceutical compounds which are able to suppress activation of the HIV LTR promoter in cells infected with HIV, iv) pharmaceutical compounds which are able to inhibit HIV entry into a cell, and/or v) pharmaceutical compounds which are able to prime uninfected cells to suppress HIV LTR promoter activity in response to infection by HIV.

It will be appreciated that the pharmaceutical compound of step g) may selected from the group consisting of an oncology drug or a kinase inhibitor. The oncology drug may be selected from the group of pharmaceutical compounds consisting of abiraterone, aminolevulinic acid hydrochloride, cisplatin, dactinomycin, dexrazoxane, erlotinib hydrochloride, everolimus, floxuridine, gefitinib, ifosfamide, plicamycin, temozolomide, thalidomide, vemurafenib, vincristine sulfate, vorinostat, and pharmaceutically acceptable salts thereof. In a further embodiment the kinase inhibitor may be selected from the group consisting of A-674563, AT7519, SNS-032, aurora A inhibitor I, crenolanib, foretinib, GSK2126458, NVP-BHG712, LDN193189, PIK-75, ponatinib, saracatinib, vargatef, and WZ4002.

According to a second aspect of the invention there is provided for an miRNA mimic or an miRNA inhibitor selected from the group consisting of hsa-let-7a-5p, hsa-let-7d-5p, hsa-miR-23a, hsa-miR-92a-1-5p, hsa-mir-124a-3p, hsa-miR-124a, hsa-miR-138, hsa-miR-146a, hsa-miR-149-

3p, hsa-miR-150, hsa-miR-193b-5p, hsa-miR-342-5p, hsa-miR-421, hsa-miR-423-3p, hsa-miR-509-3p, hsa-miR-637, hsa-ir-650, hsa-miR-520d-5p, hsa-miR-1908, hsa-miR-2110, hsa-miR-3162, hsa-miR-3185, hsa-miR-3189, hsa-miR-3191, hsa-miR-3191-3p, hsa-miR-4259, and hsa-miR-4314 for use in the suppression of HIV replication in a cell. A third aspect of the invention provides for an miRNA mimic or an miRNA inhibitor selected from the group consisting of hsa-mir-29c*, hsa-miR-193b-5p, hsa-miR-421, hsa-miR-1908, and hsa-miR-3189 for use in inducing apoptosis in a cell in response to HIV infection of the cell. Yet a further aspect of the invention provides for an miRNA mimic or an miRNA inhibitor selected from the group consisting of hsa-miR-34c-3p, hsa-miR-125b-5p, hsa-miR-150, hsa-miR-155, hsa-miR-200c, hsa-miR-361-5p, hsa-miR-504, hsa-miR-1200 and hsa-miR-1910 for use in increasing the level of HIV replication in a cell.

In another aspect of the invention there is provided for a compound or a pharmaceutically effective salt thereof selected from the group consisting of foretinib, GSK2126458, NVP-BHG712, ponatinib, saracatinib, temozolomide, thalidomide, vargatef, vincristine sulfate, and WZ 4002 for use in the prevention of HIV infection in a subject. In yet another aspect of the invention the compound or pharmaceutically acceptable salt thereof, is selected from the group consisting of A-674563, dactinomycin, ifosfamide, cisplatin, dexrazoxane, everolimus and vemurafenib for use in the suppression of HIV infection in an HIV infected subject. A further aspect of the invention provides for a compound or a pharmaceutically acceptable salt thereof, selected from the group consisting of A-674563, abiraterone, aminolevulinic acid hydrochloride, AT7519, aurora A inhibitor I, crenolanib, erlotinib hydrochloride, floxuridine, gefitinib, LDN193189, PIK-75, plicamycin, SNS-032, and vorinostat for use in inducing apoptosis in a cell in response to HIV infection of the cell in a subject.

BRIEF DESCRIPTION OF THE FIGURE

Non-limiting embodiments of the invention will now be described by way of example only and with reference to the following FIGURE:

FIG. 1: Agonist-Antagonist approach using miRNA mimic and inhibitor molecules

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms “a”, “an” and “the” include the plural form, unless the context clearly indicates otherwise.

The terminology and phraseology used herein is for the purpose of description and should not be regarded as limiting. The use of the terms “comprising”, “containing”, “having” and “including” and variations thereof used herein, are meant to encompass the items listed thereafter and equivalents thereof as well as additional items.

Provided herein is a high-throughput screening method for screening a library of miRNA mimics and inhibitors in 96 well plates in duplicate in an engineered reporter cell line. This engineered reporter cell line stably expresses an HIV LTR promoter upstream of hGFP. Reporter cells in experimental wells were transfected with a specific miRNA mimic or inhibitor 48 hours prior to infection with HIV. Cells were then infected with HIV for 48 hours and samples processed for imaging. Images were acquired using an automated line scanning confocal fluorescent microscope (LSM) and analysed using a suite of novel image analysis algorithms in order to identify miRNAs that were able to modulate HIV infection. The present inventors consequently identified several miRNA molecules that could be used in anti-HIV therapeutic approaches. The inventors further identified specific functional pathways enriched in the miRNA screen data. The functional pathways and miRNA targets identified by the initial screens therefore also represent potentially attractive points of intervention for targeted HIV therapies. The inventors conducted targeted drug/compound screens focused on the pathways and protein targets identified in the miRNA screens. Using this approach the inventors were able to identify a number of drugs/compounds, which are able to either suppress HIV infection or preferentially target or sensitise host cells to apoptose in response to infection by HIV. A number of these drugs have also already been approved by the FDA for use in the treatment of various forms of cancer and this should facilitate the rapid repurposing of these compounds for use as novel anti-HIV therapeutics.

The inventors have also described the use of a primary miRNA screen as a tool to identify specific therapeutically relevant functional pathways (in this case pertinent to HIV replication). This approach allows for the interogation of pharmaceutical compounds (preferbaly FDA-approved) targeted to these pathways, thus not only reducing the cost associated with large scale non-targeted compound screening but also dramatically increasing the likehood of identifying compounds that will illicit the desired biological effect.

As used herein the term “nucleic acid” refers to a deoxyribonucleotide or ribonucleotide polymer in either single- or double-stranded form, and unless otherwise limited, encompasses analogues of natural nucleotides that hybridise to nucleic acids in a manner similar to naturally occurring nucleotides. Unless otherwise indicated, a particular nucleic acid sequence includes the complementary sequence thereof.

The present invention provides nucleic acid compounds which are useful in the modulation of gene expression. The nucleic acid compounds of the invention modulate gene expression by hybridising to nucleic acid target sequences. The result of the hybridisation is the loss of normal function of the target nucleic acid. In a preferred embodiment of this invention modulation of gene expression is effected via modulation of a particular RNA associated with the particular gene-derived RNA.

As used herein “RNA interference” (RNAi) is the process by which synthetic siRNAs or the expression of a nucleic acid (including miR, siRNA, shRNA) causes sequence-specific degradation of complementary RNA, sequence-specific translational suppression or transcriptional gene silencing and further as used herein “RNAi-encoding sequence” refers to a nucleic acid sequence which, when expressed, causes RNA interference.

The abbreviation "siRNA" refers to a "small interfering RNA". siRNA's generally consist of a short double-stranded RNA molecule, the antisense- (guide) strand and the sense- (passenger) strand. Typically a siRNA molecule comprises a duplex region with 3' overhangs of 2 nucleotides. One strand is incorporated into a cytoplasmic RNA-induced silencing complex (RISC). This directs the sequence specific RNA cleavage that is effected by RISC. Mismatches between the siRNA guide and its target may cause translational suppression instead of RNA cleavage. siRNA may be synthetic or derived from processing of a precursor by Dicer.

Specifically the invention relates to the use of microRNAs (miRNAs). The miRNAs of the invention may be classified as miRNA mimics or miRNA inhibitors.

As used herein miRNA mimics refers to double-stranded, synthetic replicates of endogenous miRNAs which augment the intracellular concentration and function of a specific endogenous miRNA. miRNA inhibitors on the other hand refers to synthetic, single-stranded RNA molecules which are able to bind to endogenous target miRNAs and prevent them from regulating their mRNA targets.

The term "transcription" refers to the process of producing RNA from a DNA template. "In vitro transcription" refers to the process of transcription of a DNA sequence into RNA molecules using a laboratory medium which contains an RNA polymerase and RNA precursors and "intracellular transcription" refers to the transcription of a DNA sequence into RNA molecules, within a living cell. Further, "in vivo transcription" refers to the process of transcription of a DNA sequence into RNA molecules, within a living organism.

As used herein, the term 'target nucleic acid' or "nucleic acid target" refers to a nucleic acid sequence derived from a gene, in respect of which the RNAi encoding sequence of the invention is designed to inhibit, block or prevent gene expression, enzymatic activity or interaction with other cellular or viral factors. In terms of the invention "target nucleic acid" or "nucleic acid target" encompass any nucleic acid capable of being targeted including without limitation including DNA, RNA (including pre-mRNA and mRNA or portions thereof) transcribed from DNA, and also cDNA derived from RNA.

The present invention provides nucleic acid compounds which are useful in the modulation of gene expression. The nucleic acid compounds of the invention modulate gene expression by hybridising to nucleic acid target sequences. The result of the hybridisation is the loss of normal function of the target nucleic acid. In a preferred embodiment of this invention modulation of gene expression is effected via modulation of a particular RNA associated with the particular gene-derived RNA. The present invention further provides for pharmaceutical compounds which target the particular pathways, polynucleotides and/or polypeptides in a cell which are modulated by the nucleic acid compounds of the invention including but not limited to inhibition of cellular processes, interference with cellular processes, interruption of biosynthetic pathways, apoptosis, interference with transcription, translation and/or replication.

In the context of the present invention, "modulation" and "modulation of expression" can mean either an increase (stimulation) or a decrease (inhibition) in the level or amount of a nucleic acid molecule encoding the gene, e.g., DNA or RNA. Inhibition is often the preferred form of modulation of expression and mRNA is often a preferred target nucleic acid.

The invention also relates to repurposing pharmaceutical compounds for use in the treatment of HIV.

The term "pharmaceutically acceptable" refers to properties and/or substances which are acceptable for administration to a subject from a pharmacological or toxicological point of view. Further "pharmaceutically acceptable" refers to factors such as formulation, stability, patient acceptance and bioavailability which will be known to a manufacturing pharmaceutical chemist from a physical/chemical point of view.

The "suitable forms" of the pharmaceutical compounds may be combined with "pharmaceutically acceptable carriers" and other elements known in the art in order to ensure efficient delivery of the active pharmaceutical ingredient to a subject.

By "pharmaceutically acceptable carrier" is meant a solid or liquid filler, diluent or encapsulating substance which may be safely used for the administration of the extract, pharmaceutical composition and/or medicament to a subject.

The term "effective amount" in the context of preventing or treating a condition refers to the administration of an amount of the active pharmaceutical ingredient in a pharmaceutical compound to an individual in need of treatment, either a single dose or several doses of the pharmaceutical compound may be administered to a subject.

Although some indications have been given as to suitable dosages of the pharmaceutical compounds of the invention, the exact dosage and frequency of administration of the effective amount will be dependent on several factors. These factors include the individual components used, the formulation of the extract or pharmaceutical composition containing the extract, the condition being treated, the severity of the condition, the age, weight, health and general physical condition of the subject being treated, and other medication that the subject may be taking, and other factors as are known to those skilled in the art. It is expected that the effective amount will fall within a relatively broad range that can be determined through routine trials.

Toxicity and therapeutic efficacy of compositions of the invention may be determined by standard pharmaceutical procedures in cell culture or using experimental animals, such as by determining the LD50 and the ED50. Data obtained from the cell cultures and/or animal studies may be used to formulate a dosage range for use in a subject. The dosage of any composition of the invention lies preferably within a range of circulating concentrations that include the ED50 but which has little or no toxicity. The dosage may vary within this range depending upon the dosage form employed and the route of administration utilised. For compositions of the present invention, the therapeutically effective dose may be estimated initially from cell culture assays.

The following example is offered by way of illustration and not by way of limitation.

EXAMPLE

Cell Lines

The miRNA and targeted-drug/compound screens were performed using the engineered GHOST(3) cell line. The GHOST(3) cell line was originally derived from a Human Osteosarcoma cell line (HOS) and is available from the NIH AIDS Research and Reference Reagent Program (catalogue number. 3942). GHOST(3) cells were seeded at a density of ~6000 cells per well in uClear 96 well imaging plates (Grenier Bio-one) for all screening applications. HOS cells were stably transduced with an MV7neo-T4 retroviral vector and stably express an HIV-2 Long terminal Repeat (LTR) promoter driving and hGFP and a cytomegalovirus (CMV)

promoter driving Hygromycin B resistance (Momer et al., (1999)). Typical HIV infection in GHOST(3) cells results in the binding of the HIV trans-activating protein (tat) to the LTR promoter thus stimulating hGFP expression in infected cells. This reporter cell line has previously been shown to be sensitive to multiple HIV-1 subtypes in addition to HIV-2 and has also been validated as tool to directly assay HIV-1 infection in cultured cells (Cecilia et al., (1998)). GHOST(3) cells were cultured in Dulbecco's Minimal Essential Medium (DMEM, Invitrogen) supplemented with 10% heat-inactivated Fetal bovine serum (FBS) (Biochrom) and 1× GlutaMax, stabilized L-glutamine reagent (Invitrogen). GHOST(3) cells were cultured under antibiotic selection with Puromycin (1 ug/mL); Hygromycin B (100 ug/mL) and G418 (500 ug/mL). The human embryonic Kidney 293T (HEK293T) and JC53 cell lines were cultured in DMEM supplemented with 10% heat-inactivated Fetal bovine serum (FBS) (Biochrom) and 1× GlutaMax (Invitrogen).

miRNA Mimic and Inhibitors

The miRNA screens were conducted using the miRIDIAN® miRNA mimic and inhibitor libraries (Thermo Scientific™) based on miRBase v.16.0 (www.miRBase.org). The library was comprised of 1239 miRNA mimic molecules and 1245 miRNA inhibitor molecules. miRNA mimics are double-stranded, synthetic replicates of endogenous miRNAs and augment the intracellular concentration and function of a specific endogenous miRNA (FIG. 1). miRNA inhibitors are synthetic, single-stranded RNA molecules which are able to bind to endogenous target miRNAs and thus prevent them from regulating their mRNA targets (FIG. 1). miRNA mimic and inhibitor molecules were used at a final concentration of 25 nM and introduced into cell lines by liposome-mediated transfection using Lipofectamine RNAiMax (Invitrogen). Briefly. 2.5 uL of 1 uM miRNA mimic or inhibitor molecules were diluted to final volume of 10 uL in serum-free media (DMEM, Gibco). A volume of 0.15 uL of RNAiMax was then diluted in serum free media to a final volume of 10 uL. The 10 uL of diluted RNAiMax solution was then combined with the diluted miRNA solution and this transfection mixture was incubated at room temperature for 20 minutes. The 20 uL transfection mixture was then added directly GHOST(3) cells cultured in a well of a 96 well. Suitable control wells were included on each plate and these were used in the subsequent image analysis steps.

Targeted Drug Screens

A library of 101 Food and Drug Administration (FDA) approved oncology drugs as well as a library of 192 kinase-inhibitor compounds were screened as potential anti-HIV therapeutics using the GHOST(3) reporter cell line. Drugs were screened at 3 different concentrations of 100 nM, 1 uM and 10 uM. Each library was screened in triplicate at each drug concentration and in the following 3 formats:

i) Phenocopy Screen

This screen format was utilised to identify drugs/compounds that were able to protect host cells against HIV infection; suppress HIV replication or selectively sensitize or prime host cells to apoptose upon infection by HIV. GHOST(3) cells were seeded in the wells of a 96 well plate 24 hour prior to addition of a specific oncology drug at the appropriate concentration. Twenty-four hours post drug treatment, the drug supplemented media was removed and replaced with infective media containing the Subtype B pseudoviral strain, PSGIII. Cells were infected at an MOI of 0.5. The infective media was removed 48 hour post infection and cells were processed for imaging as previously described (See Sample Preparation).

ii) Clearance Screen

This screen format was utilised to identify drugs/compounds that were able to suppress HIV replication in host cells already infected by HIV or drugs/compounds that were able to selectively target HIV-infected cells for apoptosis. GHOST(3) cells were seeded in the wells of a 96 well plate 24 hour prior to infection with the Subtype B pseudoviral strain, PSGIII, at an MOI of 0.5. The infective media was then removed 48 hour post infection and replaced with normal culture media supplemented with a drug/compound at the appropriate concentration. Twenty-four hours post drug treatment, cells were processed for imaging as previously described.

iii) Drug Only Screen

This screen format was used as a control to identify drugs that were broadly cytotoxic. Drugs/compounds that resulted in >25% cytotoxicity compared to untreated control wells were eliminated from further analysis. GHOST(3) cells were seeded in 96 well plates, 24 hr post seeding, drugs were added to culture medium at the required final concentration. Twenty-four hours post drug treatment cells were processed for imaging as described previously.

Viral Production and Infection Assay

Subtype B viral stocks were produced by the dual transfection of HEK293T cells with a PSGIII (Subtype B) viral backbone plasmid which lacks an envelope/packaging protein and a second plasmid expressing an HIV-BAL viral envelope protein (Subtype B). Plasmid transfections were conducted using the FuGene 6 lipid-based transfection reagent (Promega) as per the manufacturer's guidelines. Viral titres were determined using a luciferase readout-assay based on the JC53 cell line and the TCID50 calculation method described by Reed and Muench (1938). GHOST(3) cells were exposed to virions at an MOI of 0.5 for both the miRNA and targeted drug/compound screens. Cells were infected in SFM supplemented with 1× Glutamax (Infecting media) as FBS has previously been described to negatively impact the infection efficiency of HIV.

Sample Preparation

Cells were Washed Twice in 1×PBS Before Fixation with a 3.7% Formaldehyde solution for 30 minutes at room temperature. Cells were washed once with 1×PBS before the addition of Hoechst Nuclear stain (Invitrogen) at 2 uM final concentration in 1×PBS for 30 minutes at room temperature. The Hoechst staining solution was aspirated and replaced with 50 uL of 1×PBS solution before imaging.

Imaging

Four fields of view (100 um apart) were acquired from the central region of each well imaged. Images were acquired in the 405 and 488 fluorescent channels for each field of view. Wells were imaged using the 20× ewld objective on the Image Xpress Ultra automated confocal microscope system (Molecular Devices). The imaging parameters were kept constant for all replicates of both miRNA and targeted drug/compound screens.

Image Analysis

HCS analyses rely on the discrimination of multiple biological descriptors between images derived from experimental and control wells for HIT identification. HCS analyses thus require the extraction quantitative, subcellular measurements (features) from the acquired images in order to identify subsets of these features that can accurately and reproducibly classify specific biological phenotypes within experimental wells.

Feature extraction algorithms were utilized in order to extract 16 subcellular measurements from the acquired images. These 16 factors are derived from 15 descriptors previously described by Genovesio et al. 2011 to be relevant indicators of the infective state of host cells, with addition of 'infection efficiency' as a descriptor of the percentage of infected cells per treatment well.

A bespoke support vector machine-learning (SVML) pattern recognition algorithm was trained to identify phenotypes of interest using the relevant control wells. Transfection of GHOST(3) with an siRNA targeting the human CD4 receptor (25 nM) 48 hours prior to exposure to HIV was shown to significantly suppress HIV infection and produce a visually distinct phenotype representative of the inhibition of HIV replication. Knockdown of the CD4 receptor required for HIV entry in GHOST(3) cells 48 hours prior to exposure to HIV resulted in suppressed GFP reporter signal and when compared to natural infection controls (high GFP signal) creates contrasting visual phenotypes required for subsequent image analysis. siCD4 wells were included on every screening plate in the miRNA screens as positive controls for suppressed HIV infection. Likewise the addition of the HIV-1 integrase inhibitor, Raltegravir (10 uM) to GHOST(3) culture medium 24 hour prior to exposure to HIV was also shown to produce a distinct phenotype representative of suppressed HIV replication. The transfection of siCD4 and Raltegravir treatment were thus utilised in the miRNA and drug/compound screens respectively as positive controls for the inhibition of HIV-1 replication.

SVML algorithms were trained using these controls and were thus able to generate a decision boundary (HIT boundary) that defines a region of 16 dimensional space which is representative of the Raltegravir or siCD4 control wells and which is also distinct from the controls representative of a natural infection phenotype. Experimental wells from the miRNA and drug screens, which were classified within the HIT boundary closer to the siCD4 and Raltegravir controls, were identified as positive HITs for the inhibition of HIV replication. miRNA mimics or inhibitors which were able to enhance activation of the HIV LTR promoter were identified by evaluating the average GFP intensity in experimental wells, relative to the natural infection controls. miRNA molecules which produced a greater than 2-fold increase in average GFP intensity relative to control wells were classified as HIV enhancer miRNA molecules. Only miRNA molecules and drugs which were shown to elicit concordant phenotypes across replicate screens were included in the final list of HITs. Additionally, using the values obtained for cell counts per well (as per Hoechst staining) we were also able to evaluate the cytoxicity of specific drugs and compounds using the "drug only" screen format as a control. Drugs/compounds which were shown to be cytotoxic specifically in response to HIV exposure in either the phenocopy and clearance screen formats but not in the drug only screens were also identified as drugs/compounds of interest.

Host miRNAs are Able to Regulate HIV Replication and Modulate Host Cell Responses to HIV Infection The use of both miRNA mimic and inhibitor molecules allowed for the parallel evaluation of both over-expression and suppression phenotypes for a given miRNA. This two-pronged functional approach allows for a robust assessment of the functional relevance of a given miRNA in context of HIV infection. The bespoke image analyses identified a number of miRNA mimic and inhibitor molecules which could potentially modulate HIV infection (See Table 1). These miRNA molecules could broadly be divided into three classes depending on their effect on host cells in response to exposure to HIV:

I. miRNA molecules which are able to inhibit HIV entry or prime uninfected cells to suppress LTR activation upon infection by HIV
II. miRNA molecules which are able to sensitize uninfected cells to apoptosis in response to infection by HIV
III. miRNA molecules which could promote activation of the HIV LTR promoter.

TABLE 1

Human microRNA mimics and inhibitors that reguate HIV replication and infection

| miRNA name | Molecule | miRNA molecule sequence | Effect[a] | miRNA Target(s) | Pathway* |
|---|---|---|---|---|---|
| hsa-let-7a-5p | Mimic | UGA GGU AGU AGG UUG UAU AGU U (SEQ ID NO: 1) | Supp | CDK6, EGFR, CDKN1A | DDR, CC, APO, PC |
| hsa-let-7d-5p | Mimic | AGA GGU AGU AGG UUG CAU AGU U (SEQ ID NO: 2) | Supp | HMGA2, H2AFX | DDR, PC |
| hsa-miR-23a | Mimic | AUC ACA UUG CCA GGG AUU UCC (SEQ ID NO: 3) | Supp | FANCG | DDR |
| hsa-mir-29c* | Mimic | UGA CCG AUU UCU CCU GGU GUU C (SEQ ID NO: 4) | Tox | BCL-xL | APO, PC |
| hsa-miR-34c-3p | Mimic | AAU CAC UAA CCA CAC GGC CAG G (SEQ ID NO: 5) | EH | MET, CDK4, BCL.2 | CC, APO, PC |
| hsa-miR-92a-1-5p | Mimic | AGG UUG GGA UCG GUU GCA AUG CU (SEQ ID NO: 6) | Supp | Unknown | PC |
| hsa-miR-124a-3p | Mimic | UAA GGC ACG CGG UGA AUG CC (SEQ ID NO: 7) | Supp | NGR1, CDK6 | DDR, PC |

TABLE 1-continued

Human microRNA mimics and inhibitors that reguate HIV replication and infection

| miRNA name | Molecule | miRNA molecule sequence | Effect[a] | miRNA Target(s) | Pathway* |
|---|---|---|---|---|---|
| hsa-miR-125b-5p | Mimic | UCC CUG AGA CCC UAA CUU GUG A (SEQ ID NO: 8) | EH | P53 | DDR, CC APO, PC |
| hsa-miR-138 | Mimic | GC UGG UGU UGU GAA UCA GGC CG (SEQ ID NO: 9) | Supp | H2AX | DDR |
| hsa-miR-146a | Mimic | UGA GAA CUG AAU UCC AUG GGU U (SEQ ID NO: 10) | Supp | BRCA1, BRCA2, ERBB4, CDKN1A | DDR, CC, PC |
| hsa-miR-149-3p | Mimic | AGG GAG GGA CGG GGG CUG UGC (SEQ ID NO: 11) | Supp | AKT1, EF2F1 | CC, PC |
| hsa-miR-150 | Inhibitor | UCU CCC AAC CCU UGU ACC AGU G (SEQ ID NO: 12) | Supp | P53 | DDR, APO, PC |
| hsa-miR-150 | Mimic | UCU CCC AAC CCU UGU ACC AGU G (SEQ ID NO: 13) | EH | P53 | DDR, APO, PC |
| hsa-miR-155 | Mimic | UUA AUG CUA AUC GUG AUA GGG GU (SEQ ID NO: 14) | EH | P53 | PC, APO |
| hsa-miR-193b-5p | Mimic | CGG GGU UUU GAG GGC GAG AUG A (SEQ ID NO: 15) | Supp, Tox | RB1, DHFR | DDR, CC, PC |
| hsa-miR-200c | Mimic | UAA UAC UGC CGG GUA AUG AUG GA (SEQ ID NO: 16) | EH | BCL-2, XIAP | DDR, APO |
| hsa-miR-342-5p | Mimic | AGG GGU GCU AUC UGU GAU UGA (SEQ ID NO: 17) | Supp | Unknown | PC |
| hsa-miR-381-5p | Mimic | UUA UCA GAPS UCU CCA GGG GUA C (SEQ ID NO: 18) | EH | Unknown | PC |
| hsa-miR-421 | Mimic | AUC AAC AGA CAU UAA UUG GGC GC (SEQ ID NO: 19) | Supp, Tox | ATM | DDR |
| hsa-miR-423-3p | Mimic | AGC UCG GUC UGA GGC CCC UCA GU (SEQ ID NO: 20) | Supp | CDKN1A | DDR, CC, PC |
| hsa-miR-504 | Mimic | AGA CCC UGG UCU GCA CUC UAU C (SEQ ID NO: 21) | EH | P53, BAX, FAS | DDR, CC, APO PC |
| hsa-miR-509-3p | Mimic | UGA UUG GUA CGU CUG UGG GUA G (SEQ ID NO: 22) | Supp | Unknown | PC |
| hsa-miR-637 | Mimic | ACU GGG GGC UUU CGG GCU CUG CGU (SEQ ID NO: 23) | Supp | SP7, STAT3, LIF | DDR, CC |
| hsa-mir-650 | Mimic | AGG AGG CAG CCC UCU CAG GAC (SEQ ID NO: 24) | Supp | NG4, NDRG2 | DDR, CC, PC |
| hsa-miR-520d-5p | Mimic | CUA CAA AGG GAA GCC CUU UC (SEQ ID NO: 25) | Supp | Unknown | PC |

TABLE 1-continued

Human microRNA mimics and inhibitors that reguate HIV replication and infection

| miRNA name | Molecule | miRNA molecule sequence | Effect[a] | miRNA Target(s) | Pathway* |
|---|---|---|---|---|---|
| hsa-miR-1200 | Mimic | CUC CUG AGC CAU UCU GAG CCU C (SEQ ID NO: 26) | EH | NEIL2 | PC |
| hsa-miR-1908 | Mimic | CGG CGG GGA CGG CGA UUG GUC (SEQ ID NO: 27) | Supp, Tox | Unknown | PC |
| hsa-miR-1910 | Mimic | CCA GUC CUG UGC CUG CCG CCU (SEQ ID NO: 28) | EH | Uknown | PC |
| hsa-miR-2110 | Mimic | UUG GGG AAA CGG CCG CUG AGU G (SEQ ID NO: 29) | Supp | Unknown | PC |
| hsa-miR-3162 | Mimic | UUA GGG AU AGA AGG GUG GGG AG (SEQ ID NO: 30) | Supp | Unknown | PC |
| hsa-miR-3185 | Mimic | AGA AGA AGG CGG UCG GUC UGC GG (SEQ ID NO: 31) | Supp | Uknown | PC |
| hsa-miR-3189 | Mimic | CCC UUG GGU CUG AUG GGG UAG (SEQ ID NO: 32) | Supp, Tox | Uknown | PC |
| hsa-miR-3191 | Mimic | UGG GGA CGU AGC UGG CCA GAC AG (SEQ ID NO: 33) | Supp | Unknown | PC |
| hsa-miR-4259 | Mimic | CAG UUG GGU CUA GGG GUC AGG A (SEQ ID NO: 34) | Supp | Unknown | PC |
| hsa-miR-4314 | Mimic | CUC UGG GAA AUG GGA CAG (SEQ ID NO: 35) | Supp | Unknown | PC |

[a]Supp = suppressed HIV replication; EH = enhanced HV replication; Tox = Toxic in response to HIV infection
*DDR = DNA damage response; CC = cell cycle; APO = apoptosis; PC = pathways in cancer Visual inspection of the experimental wells classified as HITs by our analysis confirmed that these wells were correctly classified by the analysis algorithms. miRNAs identified as inhibitory or protective against HIV were shown to be to visually similar to the siCD4 controls yielding reduced GFP reporter signal, whereas HITs identified as enhancers were shown to exhibit much stronger activation of the HIV LTR as equated to GFP signal intensity yielding significantly higher GFP reporter signal than natural infection control wells. This served as a validation of the image analysis algorithms abilities to accurately classify experimental wells relative to the HIV infective state of GHOST(3) cells.

We have uncovered a number of previously unpublished miRNA-HIV interactions and have also identified a number of miRNA-based molecules with potent anti-HIV activity whose endogenous targets and functions have not yet been elucidated. Further analysis of the miRNA HITs revealed an enrichment of miRNAs associated with a very specific subset of functional pathways. Using a combination of bioinformatics based manual searches and online databases of experimentally validated miRNA pathway and miRNA-target associations, such as miRpath (S. Vlachos et al ((2012)) and miRTarBase v.4.5 (Hsu (2011)), we were able to identify the DNA damage, cell cycle and apoptotic pathways as critical points of intervention in the HIV replicative cycle with the majority of miRNAs and miRNA targets identified in the screen shown to be functionally active in these pathways.

Characterisation of Oncogenic Traits Associated with HIV Infection

A well-characterised feature of the HIV replicative cycle involves the integration of the HIV proviral genome into host chromatin. In order to achieve this, the virus must induce a double strand break (DSB) in the host DNA and recruit host DNA repair machinery to the break sites, resulting in integration of the provirus into the host genome. DSBs are the most detrimental form of DNA lesion and as there is no intact complementary strand to serve as a template for repair, DSBs are poorly tolerated (Khanna, 2001). A single DSB is sufficient to kill yeast cells if it inactivates an essential gene, or trigger apoptosis in metazoan cells. If left uncorrected, DSBs can result in chromosomal breakage or translocations that lead to developmental defects, neurodegeneration, immunodeficiency and cancer. As the infecting virus cannot coordinate the number of integration events and consequent DSBs per host cell, HIV must have evolved a mechanism to either mask the DSB from the cell or carefully orchestrate any cellular response to the DSB to avoid triggering apoptosis. Furthermore, to induce a DSB yet ensure survival, HIV must take control of prosurvival mechanisms and suppress activation of pro-apoptotic genes.

In order to evaluate the relationship between HIV-mediated DSBs and the control of cellular DNA damage responses, we conducted 2 sets of experiments. In the first experiment, cells were treated with known DNA damage-inducing agents prior to HIV infection. Similar to cells treated only with DNA damage-inducing agents, these cells underwent complete apoptosis due to drug-induced cytotoxicity. In contrast, cells that were infected with HIV 24 hours prior to the addition of the DNA damage-inducing agents were seemingly able to evade apoptosis in spite of high levels of DNA damage. In addition, these cells stained positive for p53 serine 46, which is specifically activated in cells directed towards apoptosis, suggesting that HIV is able to evade the cellular apoptotic response by manipulating the pathway downstream of p53. These findings support the results of our miRNA screens, which suggested that HIV requires and maintains tight regulation over the DNA damage repair, cell-cycle and apoptotic pathways. Our DNA damage-inducing experimental data also suggests that HIV actively manipulates these pathways to produce a pro-survival phenotype in cells that would naturally undergo apoptosis. This cancer-like characteristic of HIV infection would thus suggest that drugs targeting pathways associated with cancers may also prove effective against HIV.

Targeted Drug Screens for the Repurposing of Existing Drugs/Compounds for the Treatment of HIV The identification numerous miRNAs and miRNA targets linked to DNA Damage Repair, cell cycle and apoptotic pathways in addition to observed cancerous nature of HIV infection in GHOST(3) suggests a close similarity between HIV-1 infection and many models of cancer. We sought to exploit this cancer-like nature of HIV via the use of a targeted screening approach based on a library of FDA-approved anticancer drugs and a library of Kinase Inhibitors. We screened these libraries using the GHOST(3) and HC screening approach that was used for the initial miRNA screens. A number of FDA approved anti-cancer compounds (Table 2.) as well a number of kinase inhibitor molecules (Table 3.) were identified as putative HITs by image analyses. Visual inspection of these HITs again confirmed that our analysis approach was able to correctly identify and classify the wells of interest. We separated the phenotypes/effects of the drugs HITs into 4 functional classes:

I. Drugs which are selectively toxic to host cells already infected by HIV

II. Drugs which are able to sensitize uninfected cells to apoptosis in response to infection by HIV III. Drugs which are able to suppress HIV LTR activity in host cells already infected with HIV IV. Drugs which are able to inhibit HIV entry or prime uninfected cells to suppress LTR activation upon infection by HIV

TABLE 2

Pharmaceutical compounds of interest

| Drug Name | Approved use | Effect* | Target or Mechanism of Action |
|---|---|---|---|
| A-674563 | Kinase inhibitor | Suppressed HIV[b] & Toxic in response to HIV[a] | A-674563 is a potent selective protein kinase B/Akt inhibitor with an IC50 of 14 nM. |
| Abiraterone | Oncology | Toxic in response to HIV[a] | Androgen biosynthesis inhibitor, which inhibits 17α hydroxylase |
| Aminolevulinic acid hydrochloride | Oncology | Toxic in response to HIV[a] | A metabolic precursor of protoporphyrin IX (PpIX), which is a photosensitizer |
| AT7519 | Kinase inhibitor | Toxic in response to HIV[a] | CDK1/cyclinB, CDK2/CyclinA, CDK2/Cyclin E, CDk4/CyclinD1, CDK6/Cyclin D3, CDk5/p35. |
| Aurora A Inhibitor I | Kinase inhibitor | Toxic in response to HIV[a] | (Aurora A: IC50 at 0.0034 μM; Aurora B: IC50 at 3.4 μM), (B/A ratio = 1000). |
| BIBF1120 (Vargatef) | Kinase inhibitor | Suppressed HIV[a] | (VEGFR), PDGFR and FGFR kinase inhibitor to VEGFR1, VEGFR2, VEGFR3 with IC50 of 34, 13 and 13 nM, respectively. |
| Cisplatin | Oncology | Suppressed HIV[b] | Platinum-containing drug that reacts in vivo by binding to and causing crosslinking of DNA, which ultimately triggers apoptosis |
| Crenolanib (CP-868596) | Kinase inhibitor | Toxic in response to HIV[a] | Potent PDGFR-α inhibitor with IC50 of 0.9 and 1.8 nM against PDGFRα and PDGFRβ, respectively. |
| Dactinomycin | Oncology | Suppressed HIV[b] | Good evidence exists that this drug bind strongly, but reversibly, to DNA, interfering with synthesis of RNA (prevention of RNA polymerase elongation) and, consequently, with protein synthesis. |
| Dexrazoxane | Oncology | Suppressed HIV[b] | Ring-opened bidentate chelating agent that chelates to free iron and interferes with iron-mediated free radical generation |
| Erlotinib hydrochloride | Oncology | Toxic in response to HIV[a] | The mechanism of clinical antitumor action of erlotinib is not fully characterized. Erlotinib inhibits the intracellular phosphorylation of tyrosine |

TABLE 2-continued

Pharmaceutical compounds of interest

| Drug Name | Approved use | Effect* | Target or Mechanism of Action |
|---|---|---|---|
| | | | kinase associated with the epidermal growth factor receptor (EGFR) |
| Everolimus | Oncology | Suppressed HIV[b] | Inhibitor of mammalian target of rapamycin (MTOR) |
| Floxuridine | Oncology | Toxic in response to HIV[a] | The primary effect is interference with DNA synthesis and to a lesser extent, inhibition of RNA formation through the drug's incorporation into RNA, thus leading to the production of fraudulent RNA. Fluorouracil also inhibits uracil riboside phophorylase, which prevents the utilization of preformed uracil in RNA synthesis |
| Foretinib | Kinase inhibitor | Suppressed HIV[a] | MET and VEGFR2/KDR kinases inhibitor with an IC50 of 0.4 and 0.8 nM for MET and KDR, respectively. |
| Gefitinib | Oncology | Toxic in response to HIV[a] | Inhibits the epidermal growth factor receptor (EGFR) tyrosine kinase by binding to the adenosine triphosphate (ATP)-binding site of the enzyme |
| GSK2126458 | Kinase inhibitor | Suppressed HIV[a] | Highly potent PI3K and mTOR inhibitor with an app Ki of 19 pM for PI3K. |
| Ifosfamide | Oncology | Suppressed HIV[b] | The cytotoxic action is primarily through the alkylation of DNA, done by attaching the N-7 position of guanine to its reactive electrophilic groups. The formation of inter- and intra- strand cross-links in the DNA results in cell death. |
| LDN193189 | Kinase inhibitor | Toxic in response to HIV[a] | BMP inhibitor with IC50 of 5 and 30 nM for ALK2 and ALK3, respectively. |
| NVP-BHG712 | Kinase inhibitor | Suppressed HIV[a] | EphB4, VEGFR2, c-raf, c-src and c-Abl kinase inhibitor with ED50 of 25 nM, 4.2, 0.4, 1.3 and 1.7 μM, respectively. |
| PIK-75 | Kinase inhibitor | Toxic in response to HIV[a] | p110α/γ forms of PI3K inhibitor with IC50 of 6, 1300, 76, 510 nM for p110α, p110β, p110γ, p110δ, respectively. |
| Plicamycin | Oncology | Toxic in response to HIV[a] | Antineoplastic antibiotic produced by *Streptomyces plicatus*, Plicamycin is presumed to inhibit cellular and enzymic RNA synthesis by forming a complex with DNA. Plicamycin may also lower calcium serum levels by inhibiting the effect of parathyroid hormone upon osteoclasts or by blocking the hypercalcemic action of pharmacologic doses of vitamin D |
| Ponatinib | Kinase inhibitor | Suppressed HIV[a] | pan-BCR-ABL, mutated form, VEGFR2, FGFR1, PDGFRα, mutant FLT3 phosphorylation and LYN. |
| Saracatinib | Kinase inhibitor | Suppressed HIV[a] | Dual-specific Src/Abl kinase inhibitor with IC50 of 2.7 and 30 nM for c-Src and Abl kinase, respectively. |
| SNS-032 (BMS-387032) | Kinase inhibitor | Toxic in response to HIV[a] | (CDK) 9, 7 and 2 inhibitor with IC50 of 4, 62 and 38 nM for CDK9, CDK2/cyclin A and CDK7/Cyclin H. |
| Temozolomide | Oncology | Suppressed HIV[a] | Undergoes spontaneous intracellular conversion via hydrolysis into a potent methylating agent, MTIC.4 MTIC methylates a number of nucleobases, most important, the guanine base. This results in the formation of nicks in the DNA, followed by apoptosis, because cellular repair mechanisms are unable to adjust to the methylated base |
| Thalidomide | Oncology | Suppressed HIV[a] | Thalidomide can directly inhibit angiogenesis induced by beg or VEGF, Derivative Pomalidomide approved by FDA in 2013 |
| Vemurafenib | Oncology | Suppressed HIV[b] | Inhibitor of the activity of some forms of the mutant BRAF protein, including BRAF V600E |
| Vincristine sulfate | Oncology | Suppressed HIV[a] | Inhibitor of mitosis at metaphase through its interaction with tubulin. Like other vinca alkaloids, Vincristine may |

TABLE 2-continued

| Pharmaceutical compounds of interest | | | |
|---|---|---|---|
| Drug Name | Approved use | Effect* | Target or Mechanism of Action |
| | | | also interfere with: 1) amino acid, cyclic AMP, and glutathione metabolism, 2) calmodulin-dependent Ca2+-transport ATPase activity, 3) cellular respiration, and 4) nucleic acid and lipid biosynthesis. |
| Vorinostat | Oncology | Toxic in response to HIV[a] | Inhibits the enzymatic activity of histone deacetylases HDAC1, HDAC2 and HDAC3 (Class I) and HDAC6 (Class II) at nanomolar concentrations (IC50 < 86 nM). |
| WZ4002 | Kinase inhibitor | Suppressed HIV[a] | EGFR T790M inhibitor(IC50 < 20 nM). |

*Key to Drug Effect Phenotypes:
Suppressed HIV[a] = in Phenocopy Screen (Protects against infection, suppresses new infections)
Suppressed HIV[b] = in Clearance Screen (Suppresses established infection)
Toxic in response to HIV[a] = in Phenocopy Screen (Sensitization of host cells to apoptosis in response to HIV infection)

GHOST(3) cells treated with the drugs/compounds of interest surprisingly revealed reduced levels of GFP-reporter signal in both stably infected HIV cells as well naïve cells treated prior to exposure to HIV. Briefly a number of drugs/compounds were identified which were able to suppress HIV replication as well target HIV infected cells for apoptosis.

The pathways and targets of the HITs identified by the drug/compound screens also showed a strong overlap with the pathways and targets identified in the miRNA screens. These findings again support the notion that specific signalling cascades or nodes within the DNA damage response, cell cycle and apoptotic pathways may prove highly effective as targets for host-directed anti-HIV ART intervention strategies.

REFERENCES

Azuma-Mukai, A., et al. Proc Natl Acad Sci USA, 2008. 105(23): p. 7964-9.
Baek, D., et al. Nature, 2008. 455(7209): p. 64-71.
Barbato, C., et al. J Biomed Biotechnol, 2009. 2009: p. 803069.
Cecilia, D., et al. Journal of Virology. 1998 72(9): 6988-6996.
Cullen, B. R. Nat Immunol, 2013. 14(3): p. 205-10.
Farh, K. K., et al. Science, 2005. 310(5755): p. 1817-21.
Ebert, M. S. and P. A. Sharp. Cell, 2012. 149(3): p. 515-24.
Fire, A. et al. Nature, 1998. 391(6669): p. 806-11.
Genovesio, A. Journal of Biomolecular Screening. 2011 16(9): 945-958.
Hsu, S.-D. Nucleic Acids Research, 2011 39 (SUPPL. 1), pp. D163-D169
Lander, E. S., et al. Nature, 2001. 409(6822): p. 860-921.
Lee, Y., et al. EMBO J, 2004. 23(20): p. 4051-60.
Lee, Y., et al. EMBO J, 2002. 21(17): p. 4663-70.
Lim, L. P., et al. Nature, 2005. 433(7027): p. 769-73.
Liu, J., et al. Science, 2004. 305(5689): p. 1437-41.
Martinez, J. and T. Tuschl. Genes Dev, 2004. 18(9): p. 975-80.
Morner, A., et al. Journal of Virology. 1999 73(3): 2343-2349.
Ponting, C. P. and T. G. Belgard. Hum Mol Genet, 2010. 19(R2): p. R162-8.
Reed, L. J. and Muench, H. The American Journal of Hygiene. 1938: 27: p 493-497.
S. Vlachos, N. et al. Nucleic Acids Research 2012. 40: W498-504.
Yamada, K. et al. Science, 2003. 302(5646): p. 842-6.
Yekta, S. Science, 2004. 304(5670): p. 594-6.

The invention claimed is:

1. A method of inhibiting HIV entry or priming uninfected cells to suppress LTR activation upon infection by HIV in a subject comprising administering an anti-cancer compound or a pharmaceutically acceptable salt thereof to the subject, wherein the anti-cancer compound or pharmaceutically effective salt thereof is foretinib, 2,4-difluoro-N-[2-methoxy-5-(4-pyridazin-4-ylquinolin-6-yl)pyridin-3-yl]benzenesulfonamide, 4-methyl-3-[(1-methyl-6-pyridin-3-ylpyrazolo[3,4-d]pyrimidin-4-yl)amino]-N-[3-(trifluoromethyl)phenyl]benzamide, ponatinib, saracatinib, vargatef, and/or N-(3-(5-chloro-2-(2-methoxy-4-(4-methylpiperazin-1-yl)phenylamino)pyrimidin-4-yloxy)phenyl)acrylamide.

2. A method of treating HIV infection in a subject comprising administering an anti-cancer compound or a pharmaceutically acceptable salt thereof to the subject, wherein the anti-cancer compound or pharmaceutically effective salt thereof suppresses HIV LTR activity and/or induces apoptosis in a cell in response to HIV infection of the cell, wherein the anti-cancer compound or pharmaceutically acceptable salt thereof that suppresses HIV LTR activity is (2S)-1-[5-(3-methyl-2H-indazol-5-yl)pyridin-3-yl]oxy-3-phenylpropan-2-amine, dexrazoxane, everolimus, and/or vemurafenib, and wherein the anti-cancer compound or pharmaceutically acceptable salt thereof that induces apoptosis in a cell in response to HIV infection of the cell is (2S)-1-[5-(3-methyl-2H-indazol-5-yl)pyridin-3-yl]oxy-3-phenylpropan-2-amine, abiraterone, 4-[(2,6-dichlorobenzoyl)amino]-N-piperidin-4-yl-1H-pyrazole-5-carboxamide, N-(2-Chlorophenyl)-4-(2-(4-(2-(4-ethylpiperazin-1-yl)-2-oxoethyl)phenylamino)-5-fluoropyrimidin-4-ylamino)benzamide, crenolanib, gefitinib, 4-[6-(4-piperazin-1-ylphenyl)pyrazolo[1,5-a]pyrimidin-3-yl]quinoline, N-[(6-bromo-3-imidazo[1,2-a]pyridinyl)methylideneamino]-N,2-dimethyl-5-nitrobenzenesulfonamide, plicamycin, and/or N-[5-[(5-tert-butyl-1,3-oxazol-2-yl)methylsulfanyl]-1,3-thiazol-2-yl]piperidine-4-carboxamide.

3. The method of claim 1, wherein the anti-cancer compound is foretinib.

4. The method of claim 1, wherein the anti-cancer compound is 2,4-difluoro-N-[2-methoxy-5-(4-pyridazin-4-ylquinolin-6-yl)pyridin-3-yl]benzenesulfonamide.

5. The method of claim 1, wherein the anti-cancer compound is 4-methyl-3-[(1-methyl-6-pyridin-3-ylpyrazolo[3,4-d]pyrimidin-4-yl)amino]-N-[3-(trifluoromethyl)phenyl]benzamide.

6. The method of claim 1, wherein the anti-cancer compound is ponatinib.

7. The method of claim 1, wherein the anti-cancer compound is saracatinib.

8. The method of claim 1, wherein the anti-cancer compound is N-(3-(5-chloro-2-(2-methoxy-4-(4-methylpiperazin-1-yl)phenylamino)pyrimidin-4-yloxy)phenyl)acrylamide.

9. The method of claim 2, wherein the anti-cancer compound that suppresses HIV LTR activity is (2S)-1-[5-(3-methyl-2H-indazol-5-yl)pyridin-3-yl]oxy-3-phenylpropan-2-amine.

10. The method of claim 2, wherein the anti-cancer compound suppresses HIV LTR activity and is dexrazoxane.

11. The method of claim 2, wherein the anti-cancer compound suppresses HIV LTR activity and is everolimus.

12. The method of claim 2, wherein the anti-cancer compound suppresses HIV LTR activity and is vemurafenib.

13. The method of claim 2, wherein the anti-cancer compound induces apoptosis in the cell and is (2S)-1-[5-(3-methyl-2H-indazol-5-yl)pyridin-3-yl]oxy-3-phenylpropan-2-amine.

14. The method of claim 2, wherein the anti-cancer compound induces apoptosis in the cell and is abiraterone.

15. The method of claim 2, wherein the anti-cancer compound induces apoptosis in the cell and is 4-[(2,6-dichlorobenzoyl)amino]-N-piperidin-4-yl-1H-pyrazole-5-carboxamide.

16. The method of claim 2, wherein the anti-cancer compound induces apoptosis in the cell and is N-(2-chlorophenyl)-4-(2-(4-(2-(4-ethylpiperazin-1-yl)-2-oxoethyl)phenylamino)-5-fluoropyrimidin-4-ylamino)benzamide.

17. The method of claim 2, wherein the anti-cancer compound induces apoptosis in the cell and is crenolanib.

18. The method of claim 2, wherein the anti-cancer compound induces apoptosis in the cell and is gefitinib.

19. The method of claim 2, wherein the anti-cancer compound that induces apoptosis in the cell is 4-[6-(4-piperazin-1-ylphenyl)pyrazolo[1,5-a]pyrimidin-3-yl]quinoline.

20. The method of claim 2, wherein the anti-cancer compound induces apoptosis in the cell and is N-[(6-bromo-3-imidazo[1,2-a]pyridinyl)methylideneamino]-N,2-dimethyl-5-nitrobenzenesulfonamide.

21. The method of claim 2, wherein the anti-cancer compound induces apoptosis in the cell and is plicamycin.

22. The method of claim 2, wherein the anti-cancer compound induces apoptosis in the cell and is N-[5-[(5-tert-butyl-1,3-oxazol-2-yl)methylsulfanyl]-1 3-thiazol-2-yl]piperidine-4-carboxamide.

* * * * *